United States Patent
Wictor et al.

(10) Patent No.: US 12,312,252 B2
(45) Date of Patent: May 27, 2025

(54) METHOD AND AN APPARATUS FOR EVALUATING A CONDITION OF A WATER PURIFICATION SYSTEM

(71) Applicants: BAXTER INTERNATIONAL INC., Deerfield, IL (US); BAXTER HEALTHCARE SA, Glattpark (CH)

(72) Inventors: Per-Ola Wictor, Stehag (SE); Carl-Henry Örndal, Eslöv (SE); Henrik Lindgren, Genarp (SE); Anders Wellings, Bellair Beach, FL (US); Edward Szpara, Saint Charles, IL (US)

(73) Assignee: Gambro Lundia AB, Lund (SE)

( * ) Notice: Subject to any disclaimer, the term of this patent is extended or adjusted under 35 U.S.C. 154(b) by 508 days.

(21) Appl. No.: 17/054,891

(22) PCT Filed: May 9, 2019

(86) PCT No.: PCT/EP2019/061934
§ 371 (c)(1),
(2) Date: Nov. 12, 2020

(87) PCT Pub. No.: WO2019/219502
PCT Pub. Date: Nov. 21, 2019

(65) Prior Publication Data
US 2021/0363030 A1    Nov. 25, 2021

(30) Foreign Application Priority Data
May 15, 2018 (SE) .................................... 1850557-8

(51) Int. Cl.
*C02F 1/00* (2023.01)
*A61M 1/14* (2006.01)
(Continued)

(52) U.S. Cl.
CPC ........... *C02F 1/008* (2013.01); *A61M 1/1524* (2022.05); *A61M 1/155* (2022.05);
(Continued)

(58) Field of Classification Search
CPC ........ C02F 1/008; C02F 1/441; C02F 1/4691; C02F 1/002; C02F 1/02; C02F 1/283;
(Continued)

(56) References Cited

U.S. PATENT DOCUMENTS 5,431,811 A * 7/1995 Tusini ................. A61M 1/1672
604/6.09
5,476,592 A * 12/1995 Simard ................ B01D 61/146
210/93

(Continued)

OTHER PUBLICATIONS

International Search Report; International Application No. PCT/EP2019/061934 mailed Jun. 26, 2019—3 Pages.
(Continued)

*Primary Examiner* — Akash K Varma
(74) *Attorney, Agent, or Firm* — K&L Gates LLP (57) ABSTRACT

A method and apparatus for evaluating a condition of a water purification system (40, 110) comprising a water purification apparatus (110) arranged to output purified water through an outlet (128) and through at least one sterilizing grade filter (70a, 70b) of a line set (40) fluidly connected to the outlet (128), the method comprises: monitoring a flow rate (S1) correlated with the flow rate of the purified water flowing through the at least one sterilizing grade filter (70a, 70b); monitoring a pressure (S2) correlated with the pressure of the purified water flowing to the at least one sterilizing grade filter (70a, 70b); and evaluating (S3) a condition of the water purification system based on a relationship between the monitored flow rate and the monitored pressure.

17 Claims, 6 Drawing Sheets

(51) Int. Cl.
*A61M 1/16* (2006.01)
*C02F 1/44* (2023.01)

(52) U.S. Cl.
CPC ........ *A61M 1/1561* (2022.05); *A61M 1/1672* (2014.02); *C02F 1/441* (2013.01); *A61M 1/1565* (2022.05); *A61M 1/1566* (2022.05); *A61M 1/159* (2022.05); *A61M 2205/18* (2013.01); *A61M 2205/3334* (2013.01); *A61M 2205/705* (2013.01); *A61M 2205/707* (2013.01); *C02F 2209/03* (2013.01); *C02F 2209/40* (2013.01); *C02F 2209/445* (2013.01); *C02F 2303/04* (2013.01)

(58) Field of Classification Search
CPC .. C02F 1/4695; C02F 1/00; C02F 1/44; C02F 1/28; C02F 1/469; C02F 2209/03; C02F 2209/40; C02F 2209/445; C02F 2209/05; C02F 2209/001; C02F 2209/003; C02F 2209/006; C02F 2209/008; C02F 2303/04; C02F 2101/306; C02F 2301/046; C02F 9/00; B01D 61/12; B01D 61/32; B01D 61/24; B01D 65/102; B01D 65/104; A61M 1/1672; A61M 1/1656; A61M 1/1601; A61M 1/16; A61M 2205/18; A61M 2205/3334; A61M 2205/705; A61M 2205/707; A61M 2205/3331
USPC ........................................................ 210/645
See application file for complete search history.

(56) References Cited

U.S. PATENT DOCUMENTS

| 2011/0284377 | A1 | 11/2011 | Rohde |
| 2014/0018727 | A1* | 1/2014 | Burbank ............... A61M 1/166 604/28 |
| 2016/0046503 | A1* | 2/2016 | Hoek ...................... C02F 1/004 210/741 |
| 2017/0302022 | A1 | 10/2017 | Esmail |

OTHER PUBLICATIONS

Written Opinion of the International Searching Authority; International Application No. PCT/EP2019/061934 mailed Jun. 26, 2019—6 Pages.

* cited by examiner

METHOD AND AN APPARATUS FOR EVALUATING A CONDITION OF A WATER PURIFICATION SYSTEM

PRIORITY CLAIM

The present application is a National Phase of International Application No. PCT/EP2019/061934, filed May 9, 2019, which claims priority to Swedish Application No. 1850557-8, filed May 15, 2018, the entire contents of each of which are incorporated herein by reference and relied upon.

TECHNICAL FIELD

The present disclosure relates to the field of water purification, and in particular to a method and an apparatus for evaluating a condition of a water purification system comprising a water purification apparatus and at least one sterilizing grade filter. The disclosure also relates to a data processing device, a computer program product and a computer-readable data carrier.

BACKGROUND

In treatments for kidney disease, solutes are removed from the blood by diffusion and/or convection. Diffusion is accomplished by adding a dialysate to the fluid side of a filter, for example during hemodialysis. Also during peritoneal dialysis (PD), solutes are removed from the patient through diffusion by adding a PD-solution to the peritoneum. Convection is accomplished by ultrafiltration during hemofiltration, where large volumes of fluid are withdrawn from the blood of the patient. Replacement fluid may then be added to the blood. Hemodiafiltration is a combination of hemodialysis and hemofiltration.

Thus, treatments for kidney disease often require large amounts of fluid such as dialysate, PD solution or replacement solution. The fluid should be very clean, e.g. sterile. The sterile fluid may be produced in advance and transported to the point of care in fluid tight containers. However, the containers may be heavy for the user to carry and the distribution work is comprehensive. To enhance the treatment possibilities, water from a local water supply such as the tap may be purified and mixed with concentrates to create the needed fluid at the point of treatment. The tap water may be purified on demand, according to the treatment need of the patient, by means of a water purification apparatus located at the point of treatment.

However, the purified water from the water purification apparatus may still carry some bioburden that needs to be removed with one or several sterilizing grade filters prior to mixing with sterile concentrates. Under normal use conditions the sterilizing grade filters should be able to handle the bioburden levels coming from the water purification apparatus and complete a therapy without passing any microorganisms or become clogged. The local supply of purified water has to be periodically tested to check the bioburden. However, such periodic microbial testing is costly and the quality of the water may change in between tests.

From US2014/0018727A1 it is known to test a sterile filter for leaks by performing a bubble point test or pressure decay test. The tests are performed by pumping air through the filter to determine if the integrity of a sterile filter is within expected limits. However, these tests are made after making a batch of dialysis fluid.

SUMMARY

If the tap water contains more microorganisms than the water purification apparatus is designed to handle, the sterilizing grade filters might become more clogged than expected and the water purification apparatus cannot output purified water as expected. Also, if the sterilizing grade filters have a leak, the quality of the purified water cannot be guaranteed.

It is an objective of the disclosure to alleviate at least some of the drawbacks with the prior art. It is a further objective to provide a method that evaluates if the water purification apparatus can handle the present bioburden caused by the feed water presently supplied to the apparatus.

These objectives and others are at least partly achieved by the method and apparatus according to the independent claims, and by the embodiments according to the dependent claims.

According to one aspect, the disclosure relates to a method for evaluating a condition of a water purification system comprising a water purification apparatus arranged to output purified water through an outlet port and through at least one sterilizing grade filter of a line set fluidly connected to the outlet port. The method comprises monitoring a flow rate correlated with the flow rate of the purified water flowing through the at least one sterilizing grade filter, and monitoring a pressure correlated with the pressure of the purified water flowing to the at least one sterilizing grade filter. The method also comprises evaluating a condition of the water purification system based on a relationship between the monitored flow rate and the monitored pressure.

The method provides online monitoring for excessive bioburden of a water purification system. No extra hardware is required, and the cost becomes low compared to manual testing of the bioburden of each distributed apparatus.

According to some embodiments, the relationship indicates a permeability property of the at least one sterilizing grade filter and/or a bioburden of the water purification apparatus. Thus, the permeability of the at least one sterilizing grade filter and the bioburden of the apparatus may be monitored online.

According to some embodiments, the relationship is a ratio of monitored flow rate to monitored pressure. Alternatively, the relationship is a ratio of monitored pressure to monitored flow rate. Thus, both changes of the flow rate and the pressure are considered. There is thus no need to keep the flow rate or pressure stable while monitoring the other, to get reliable data. Thereby, online monitoring during actual production of purified water is made possible.

According to some embodiments, the method comprises evaluating the condition of the water purification system based on whether the relationship fulfils one or more system dysfunction criteria. The relationship may thus be a ratio or a slope value of a curve as a function of the ratio versus time. Thereby, it can be established if the system is dysfunctional or not.

According to some embodiments, wherein the one or more system dysfunction criteria comprise that the ratio exceeds an upper ratio limit indicating the condition that the at least one sterilizing grade filter leaks, or goes below a lower ratio limit indicating the condition that the at least one sterilizing grade filter is clogged and the bioburden of the water purification apparatus is too large. Thereby the condition of the system may continuously be determined, and appropriate action can be taken if needed.

According to some embodiments, the evaluating comprises determining a slope value of a curve of a function of a ratio of monitored flow rate to monitored pressure versus time, and wherein the one or more system dysfunction criteria comprises that the slope value goes beyond one or more slope limit values. Thereby it may early be established if the system is dysfunctional, as a slope change indicating a malfunction may occur at an earlier stage than the curve amplitude goes beyond any limit value.

According to some embodiments, the one or more system dysfunction criteria include that the slope value is positive and is greater than a positive lower slope limit value, and wherein the evaluating comprises determining the condition that the at least one sterilizing grade filter leaks, upon determining that the slope value is positive and is greater than the positive lower slope limit value. Thereby it may early be established if the at least one sterilizing grade filter leaks, as a slope change indicating a leak may occur at an earlier stage than the curve amplitude goes beyond any limit value.

According to some embodiments, the one or more system dysfunction criteria include that the slope value is negative and is less than a first negative slope limit value, and wherein the evaluating comprises determining the condition that the at least one sterilizing grade filter is or will be clogged to a first degree and the bioburden of the water purification apparatus is too large, upon determining that the slope value is negative and is less than the first negative slope limit value. Thereby it may early be established if the bioburden is too large, as a slope change indicating an excess bioburden may occur at an earlier stage than the curve amplitude goes beyond any limit value.

According to some embodiments, the one or more system dysfunction criteria include that the slope value is negative and is less than a second negative slope limit value, wherein the second negative slope limit value is less than the first negative slope limit value. The evaluating comprises determining the condition that the at least one sterilizing grade filter is or will be clogged to a second degree and the bioburden of the water purification apparatus is too large, upon determining that the slope value is negative and is less than the second negative slope limit value. Thereby it may very early be established if the bioburden is too large, as a slope change indicating an excess bioburden may occur at an earlier stage than the curve amplitude goes beyond any limit value.

According to some embodiments, the evaluating comprises calculating a sum of one or several areas of a curve of a function of ratio values of monitored flow rate to monitored pressure versus time, wherein the one or more system dysfunction criteria includes that the sum is greater than a positive area limit value. The method also includes determining the condition that the at least one filter leaks, upon determining that the sum is greater than the positive area limit value. Thereby incidents such as an accidental step on the line set giving rise to an oscillation will be removed from the analysis, as it is required that the sum is greater than a certain value.

According to some embodiments, the evaluating comprises determining a ratio of monitored flow rate to monitored pressure, detecting a change of the ratio above a predetermined level and determining whether the ratio before the change is equal within an interval to the ratio after the change. The method further comprises determining the condition that the at least one filter leaks, upon determining that the ratio before the change is not equal within an interval to the ratio after the change. Thereby incidents such as an accidental step on the line set giving rise to an oscillation will be removed from the analysis, as it is required that the ratio does not return to a regular value after for example an oscillation.

According to some embodiments, the monitoring a flow rate comprises measuring a plurality of flow rate values of the purified water. Thus, a continuous monitoring is enabled.

According to some embodiments, the monitoring a pressure comprises measuring a plurality of pressure values of the purified water. Thus, a continuous monitoring is enabled.

According to some embodiments, the method comprises presenting the condition of the water purification system on a display. Thereby the user may be enabled to continuously monitor the status, or at least be noticed of the condition.

According to some embodiments, the method comprises activating an alarm upon the relationship fulfils one or more system dysfunction criteria. Thereby the user may be noticed of the dysfunction.

According to some embodiments, the method comprises stopping outputting purified water through the outlet port upon the relationship fulfils one or more system dysfunction criteria. Thereby it can be secured that no water with insufficient purity is delivered.

According to a second aspect, the disclosure relates to a data processing device comprising means, including a processor, configured for performing the method according to any of the embodiments as disclosed herein.

According to a third aspect, the disclosure relates to a computer program product comprising instructions which, when the program is executed by a control unit, cause the control unit to carry out the method according to any of the embodiments as disclosed herein.

According to a fourth aspect, the disclosure relates to a computer-readable data carrier having stored thereon the computer program according to the third aspect.

According to a fifth aspect, the disclosure relates to a water purification apparatus arranged to output purified water through an outlet port and through at least one sterilizing grade filter of a line set fluidly connected to the outlet port, the water purification apparatus comprises a control unit that is configured to: monitor, by means of a flow rate sensor, a flow rate correlated with the flow rate of the purified water flowing through the at least one sterilizing grade filter and monitor, by means of a pressure sensor, a pressure correlated with the pressure of the purified water flowing to the at least one sterilizing grade filter. The control unit is also configured to evaluate a condition of the water purification apparatus or the at least one sterilizing grade filter based on a relationship between the monitored flow rate and the monitored pressure.

According to some embodiments, the relationship indicates a permeability property of the at least one sterilizing grade filter and/or a bioburden of the water purification apparatus.

According to some embodiments, the relationship is a ratio of monitored flow rate to monitored pressure.

According to some embodiments, the control unit is configured to evaluate the condition of the water purification system based on whether the relationship fulfils one or more system dysfunction criteria.

According to some embodiments, the one or more system dysfunction criteria comprise that the ratio exceeds an upper ratio limit indicating the condition that the at least one sterilizing grade filter leaks, or goes below a lower ratio limit indicating the condition that the at least one sterilizing grade filter is clogged and the bioburden of the water purification apparatus is too large.

According to some embodiments, the control unit is configured to determine a slope value of a curve of a function of a ratio of monitored flow rate to monitored pressure, and wherein the one or more system dysfunction criteria comprises that the slope value goes beyond one or more slope limit values.

According to some embodiments, the one or more system dysfunction criteria include that the slope value is positive and is greater than a positive lower slope limit value, and wherein the control unit is configured to determine the condition that the at least one sterilizing grade filter leaks, upon determining that the slope value is positive and is greater than the positive lower slope limit value.

According to some embodiments, the one or more system dysfunction criteria include that the slope value is negative and is less than a first negative slope limit value, and wherein the control unit is configured to determine the condition that the at least one sterilizing grade filter is or will be clogged to a first degree and the bioburden of the water purification apparatus is too large, upon determining that the slope value is negative and is less than the first negative slope limit value.

According to some embodiments, the one or more system dysfunction criteria include that the slope value is negative and is less than a second negative slope limit value, wherein the second negative slope limit value is less than the first negative slope limit value. The control unit is configured to determine the condition that the at least one sterilizing grade filter is or will be clogged to a second degree and the bioburden of the water purification apparatus is too large, upon determining that the slope value is negative and is less than the second negative slope limit value.

According to some embodiments, the control unit is configured to calculate a sum of one or several areas of a curve of a function of the ratio values of monitored flow rate to monitored pressure versus time, wherein the one or more system dysfunction criteria includes that the sum is greater than a positive area limit value, and to determine the condition that the at least one filter leaks, upon determining that the sum is greater than the positive area limit value.

According to some embodiments, the control unit is configured to determine a ratio of monitored flow rate to monitored pressure, detect a change of the ratio above a predetermined level, and wherein the one or more system dysfunction criteria includes that the ratio before the change is not equal within an interval to the ratio after the change, and determining the condition that the at least one filter leaks, upon determining that the ratio before the change is not equal within an interval to the ratio after the change.

According to some embodiments, the apparatus is arranged to measure a plurality of flow rate values of the purified water.

According to some embodiments, the apparatus is arranged to measure a plurality of pressure values of the purified water.

According to some embodiments, the control unit is configured to present the condition of the water purification system on a display.

According to some embodiments, the control unit is configured to activate an alarm upon the relationship fulfils one or more system dysfunction criteria.

According to some embodiments, the apparatus is arranged to stop outputting purified water through the outlet port upon the relationship fulfils one or more system dysfunction criteria.

DETAILED DESCRIPTION

In the following a method for evaluating a condition of a water purification system will be explained. The water purification system comprises a water purification apparatus and at least one sterilizing grade filter. The at least one sterilizing grade filter is integrated into the fluid path of a disposable line set, and the line set is connected to an outlet port of the water purification apparatus. The apparatus pushes product water (or purified water) through the at least one sterilizing grade filter for the purposes of producing sterile water for infusion. The purpose of the apparatus is to purify the feed water from the local water supply. The purified water may still carry some bioburden that needs to be removed with sterilizing grade filtering prior to mixing with for example sterile concentrates. Under normal use conditions the sterilizing grade filtering should be able to handle normal bioburden levels coming from the apparatus and complete a therapy without passing any microorganisms or clogging. If the apparatus fails to control the bioburden levels within limits, the at least one sterilizing grade filter, with proper porosity and surface area, will begin to clog and slow the flow at a given pressure of product water exiting the apparatus. Also, if a break-through (i.e. a leak) of the at least one sterilizing grade filter occurs, the flow will rapidly increase. By monitoring the flow rate of the purified water passed through the at least one sterilizing grade filter, and the pressure of the purified water passed to the at least one sterilizing grade filter, a condition of the water purification system can be evaluated. The condition is for example how well the apparatus is controlling the bioburden of the system, or the status of the permeability of the at least one sterilizing grade filter. The current condition may be used e.g. to detect if the apparatus is not controlling the bioburden sufficiently and thereby stop the water production or to detect a break-through.

Figure 1:
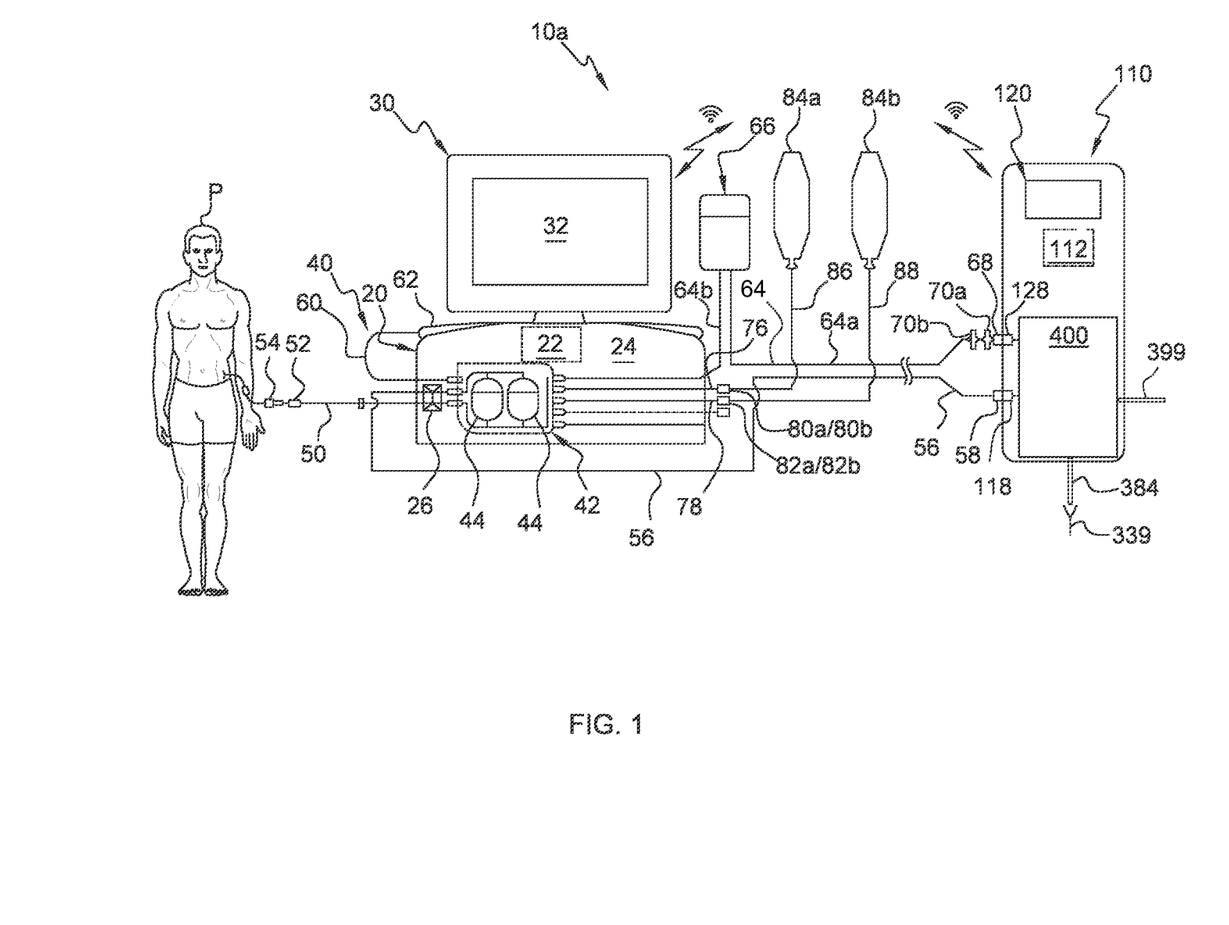
FIG. 1 illustrates a PD system according to one embodiment.

Referring now to the drawings and in particular to FIG. 1, one embodiment of a peritoneal dialysis system having point of use purified fluid production and dialysis fluid production, illustrated by system 10a. System 10a includes a cycler 20 and a water purification apparatus 110. Suitable cyclers for cycler 20 include, e.g., the Amia® or HomeChoice® cycler marketed by Baxter International Inc., with the understanding that those cyclers need updated programming to perform and use the point of use dialysis fluid produced according to system 10a. To this end, cycler 20 includes a control unit 22 having at least one processor and at least one memory. Control unit 22 further includes a wired or wireless transceiver for sending information to and receiving information from the water purification apparatus 110. The water purification apparatus 110 also includes a control unit 112 having at least one processor and at least one memory. Control unit 112 includes a wired or wireless transceiver for sending information to and receiving information from control unit 22 of cycler 20. The control unit 22 may act as a master to the control unit 112 of the apparatus 110.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purification apparatus 110 includes a first drain path 384, leading to a drain 339, which can be a housing drain or drain container. The equipment programmed via control unit 22 to prepare fresh dialysis solution at the point of use in an embodiment includes equipment for a pneumatic pumping system, including for example one or more positive pressure reservoir, one or more negative pressure reservoir, a compressor and a vacuum pump each under control of control unit 22, or a single pump creating both positive and negative pressure under control of control unit 22, for providing positive and negative pressure to be stored at the one or more positive and negative pressure reservoirs, plural pneumatic valve chambers for delivering positive and negative pressure to plural fluid valve chambers, plural pneumatic pump chambers for delivering positive and negative pressure to plural fluid pump chambers, plural electrically actuated on/off solenoid pneumatic valves under control of control unit 22 located between the plural pneumatic valve chambers and the plural fluid valve chambers, plural electrically actuated variable orifice pneumatic valves under control of control unit 22 located between the plural pneumatic pump chambers and the plural fluid pump chambers, a heater under control of control unit 22 for heating the dialysis fluid as it is being mixed in one embodiment, and an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan, which is located at the top of housing 24, beneath a heating lid (not seen in FIG. 1).

Cycler 20 in the illustrated embodiment includes a user interface 30. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button.

Water purification apparatus 110 in the illustrated embodiment also includes a user interface 120. User interface 120 may include a video monitor, which may likewise operate with a touch screen overlay placed onto video monitor for inputting commands into control unit 112. User interface 120 may also include one or more electromechanical input device, such as a membrane switch or other button. Control unit 112 may further include an audio controller for playing sound files, such as alarm or alert sounds, at one or more speaker (not shown) of water purification apparatus 110.

A disposable line set 40 is illustrated in FIG. 1, mated to cycler 20 to move fluid within the disposable line set 40, e.g., to mix dialysis fluid as discussed herein. Disposable line set 40 in the illustrated embodiment includes a disposable cassette 42, which may include a planar rigid plastic piece covered on one or both sides by a flexible membrane. The membrane pressed against housing 24 of cycler 20 forms a pumping and valving membrane. The disposable cassette 42 includes fluid pump chambers 44 that operate with the pneumatic pump chambers located at housing 24 of cycler 20 and fluid valve chambers that operate with the pneumatic valve chambers located at housing 24 of cycler 20.

The disposable line set 40 includes a patient line 50 that extends from a patient line port of cassette 42 and terminates at a patient line connector 52. The patient line connector 52 connects to a patient transfer set 54, which in turn connects to an indwelling catheter located in the peritoneal cavity of patient P. Disposable line set 40 includes a drain line 56 that extends from a drain line port of cassette 42 and terminates at a drain line connector 58. The drain line connector 58 connects removably to a drain port 118 of water purification apparatus 110.

FIG. 1 illustrates that disposable set 40 includes a first concentrate line 76 extending from a first concentrate port of cassette 42 and terminates at a first cassette concentrate connector 80a. A second concentrate line 78 extends from a second concentrate port of cassette 42 and terminates at a second cassette concentrate connector 82a.

FIG. 1 also illustrates that a first concentrate container 84a holds a first, e.g., glucose, concentrate, which is pumped from container 84a through a container line 86 to a first container concentrate connector 80b, which mates with first cassette concentrate connector 80a. A second concentrate container 84b holds a second, e.g., buffer, concentrate, which is pumped from container 84b through a container line 88 to a second container concentrate connector 82b, which mates with second cassette concentrate connector 82a.

The disposable line set 40 includes a heater/mixing line 60 that extends from a heater/mixing line port of cassette 42 and terminates at a heater/mixing bag 62. The disposable set 40 includes a water line 64. The water line 64 comprises an upstream water line segment 64a that extends to a water inlet of water accumulator 66. A downstream water line segment 64b of the water line 64 extends from a water outlet of water accumulator 66 to cassette 42. In the illustrated embodiment, upstream water line segment 64a begins at a water line connector 68 and is located upstream from water accumulator 66. The water line connector 68 is removably connected to a water outlet, i.e. the outlet port 128 of water purifier 110. The upstream water line segment 64a comprises at least one sterilizing grade filter 70a, 70b, in FIG. 1 two are depicted. However, the upstream water line segment 64a may comprise more than two sterilizing grade filters 70a, 70b, for example three, four or five sterilizing grade filters.

The water purification apparatus 110 comprises one or several purification modules 160, 170, 180 (see FIG. 2), schematically depicted 400 in FIG. 1. The apparatus 110 receives water to be purified via an inlet line 399, and outputs purified water at the outlet port 128. The apparatus 110 receives fluid to be drained at the inlet port 118, and passes the fluid to drain 339.

Figure 2:
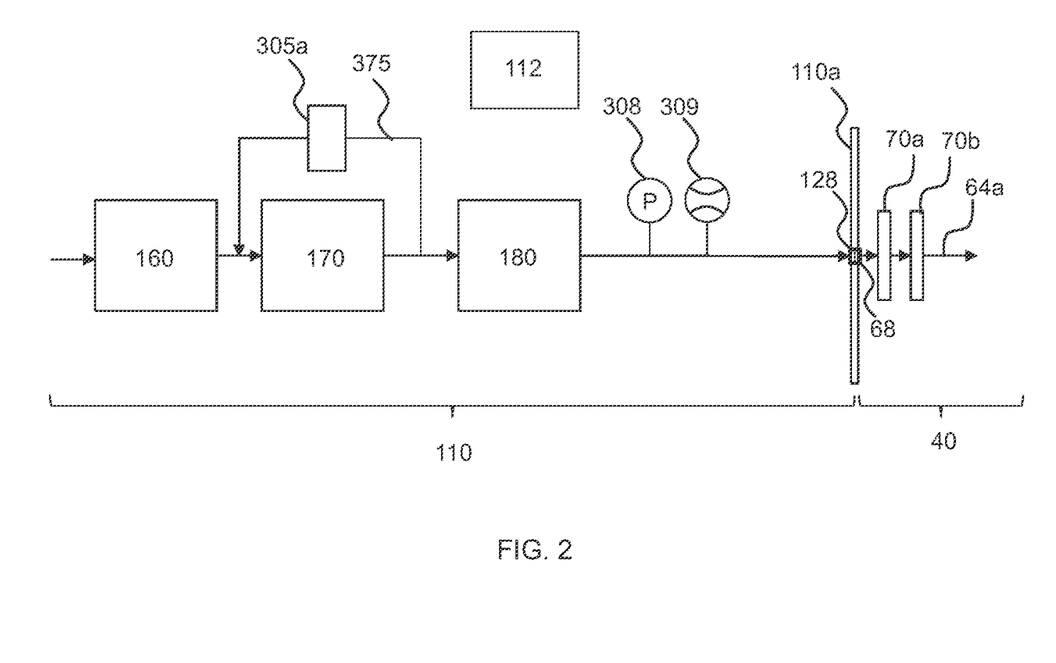
FIG. 2 is a schematic illustration of functional parts of a water purification system comprising a water purification apparatus and a line set with two sterilizing grade filters.

FIG. 2 schematically illustrates functional parts of a water purification system. The water purification system comprises a water purification apparatus 110 and a disposable line set 40 connected via a connector 40 to the outlet port 128 of the water purification apparatus 110. The water purification apparatus 110 is for example the apparatus exemplified in FIG. 1 and/or FIG. 8. The disposable line set 40 is for example the line set explained with reference to FIG. 1 and/or FIG. 8. Feed water is passed from a source of water to a pretreatment module 160 where the feed water is pre-treated with a particle filter and a bed of activated carbon. The particle filter is arranged to remove particles such as clay, silt and silicon from the incoming water. The particle filter is arranged to prohibit particles in the size of micro meter, optionally also larger endotoxin molecules, from the incoming water. The bed of activated carbon is arranged to remove chlorine and compositions with chlorine from the incoming water, and to absorb toxic substances and pesticides. In an example embodiment, the bed of activated carbon is arranged to remove one or several of hypochlorite, chloramine and chlorine. In a further example embodiment, the bed of activated carbon is also arranged to reduce organic compounds (TOC total organic carbon) including pesticides of the incoming water. The pre-treated water is passed to a reverse-osmosis (RO) module 170. The RO module 170 removes impurities such as microorganisms, pyrogens and ionic material from the pre-treated water by the effect of reverse osmosis. The pre-treated water is pressurized by a pump and forced through an RO-membrane of the RO-module to overcome the osmotic pressure. The RO-membrane is for example a semi-permeable membrane. Thereby the stream of pre-treated water is divided into a reject stream of water and a stream of permeate water. The reject water is fed to a drain and/or is recirculated to the pre-treated water. The permeate water is passed to a post-treatment module 180. The post-treatment module 180 polishes the permeate water in order to further remove ions from the permeate water, using a polisher device such as an electrically controlled deionization device, for example an Electrodeionization (EDI) device, a Capacitive Deionization (CDI) device, an Electrodialysis Reversal (EDR) device, or a polisher device such as a mixed bed filter device. The electrically controlled deionization device removes ions, from the permeate water, such as aluminum, lead, cadmium, chromium, sodium and/or potassium etc., which have passed through the RO-membrane. For example, the EDI-device utilizes electricity, ion exchange membranes and resin to deionize the permeate water and separate dissolved ions, i.e. impurities, from the permeate water. The electrically controlled deionization device produce polished water, polished by the electrically controlled deionization device to a higher purity level than the purity level of the permeate water. The deionization has an anti-bacterial effect of the product water and can reduce the amount of bacteria and endotoxins in the water due to, among other, the electrical field in the electrically controlled deionization device. The mixed bed filter device comprises a column, or container, with a mixed bed ion exchange material, and also produce polished water. The polished water, herein also referred to as product water, is thereafter ready for being delivered from an outlet port 128 of the water purification apparatus 110 to a point of use of the product water. The product water is suitable for dialysis, i.e. water for dialysis. In one embodiment, the product water is water for injection. The disposable line set 40 has at one end a water line connector 68 (that is releasably connected to the outlet port 128 of the water purification apparatus 110 for transporting the product water to a point of use. The water inlet connector 68 is arranged at an end of an upstream water line segment 64a of the disposable line set 40. The outlet port 128 is arranged in the wall 110a of the water purification apparatus 110. The disposable line set 40 here includes two sterilizing grade filters 70a, 70b arranged in the upstream water line segment 64a of the disposable line set 40, but may include only one sterilizing grade filter or more than two sterilizing grade filters. The at least one filter may be a sterile sterilizing grade filter, thus, the at least one sterilizing grade filer may itself be sterile.

The water purification apparatus 110 is arranged to output purified water through the outlet port 128 and through the at least one sterilizing grade filter 70a, 70b of the disposable line set 40 (only a part of the disposable line set 40 is shown). In an example embodiment, the at least one sterilizing grade filter 70a, 70b is arranged to filter the purified water into sterile purified water with an amount of bacteria that is zero Colony-Forming Units/mL (CFU/mL) and an amount of bacterial endotoxins that is less than 0.05 Endotoxin Units/mL (EU/mL). In other words, into sterile filtrated non-pyrogenic water, where "sterile filtrated" means zero CFU/mL. The at least one sterilizing grade filter ensures that the water used to prepare the PD fluid for administration meets requirements for sterile non-pyrogenic water. The at least one sterilizing grade filter includes a membrane having pores with average diameters suitable to produce sterile fluid, including the capability of removing endotoxins, resulting in water quality suitable for dialysis, e.g. PD. The at least one sterilizing grade filter provide the final stage of sterilization for the water that is used to mix with the one or more concentrate to provide a dialysis fluid suitable for PD. The mean pore diameter for a sterilizing grade filter may, for example, be less than one micrometer, such as 0.1-0.5 micrometer, e.g. 0.1 or 0.2 micrometer. Bacteria typically have a diameter of a few micrometers, and will then not pass through the pores. The filter membrane may further comprise a high molecular weight additive bearing cationic charges, for example a cationic charged polymer. Examples of other kinds of positively charged additives can be found in EP1710011A1. The filter membrane will thus be positively charged. The membrane will then reject bacterial endotoxins, whereby less bacterial endotoxins will pass the membrane. In an exemplary embodiment, bacteria and bacterial endotoxins will also be retained based on adsorption to the membrane. The membrane may be polyethersulfone-based. Other suitable polymers may be AN69, PAN, PMMA, cellulose etc. Suitable sterilizing grade filters 70a and 70b may, for example, be Pall IV-5 or GVS Speedflow filters, or be filters provided by the assignee of the present disclosure. In an exemplary embodiment, only one upstream or downstream sterile sterilizing grade filter 70a and 70b is needed to produce water for injection, nevertheless, here two sterilizing grade filters 70a and 70b are provided for redundancy in case one fails.

The pressure of the product water is monitored by a pressure sensor 308 arranged to detect, e.g. sense, the pressure of the product water. The flow rate of the product water is monitored by a flow rate sensor 309 arranged to detect, e.g. sense, the flow rate of the product water. The pressure and flow rate of the product water is controlled by a valve device 305a by regulating a flow rate in a recirculation path 375 recirculating part of the permeate water to the pre-treated water. The recirculation path 375 is thus fluidly connected between a point downstream the RO module 170 but upstream the post-treatment module 180, and a point upstream the RO module 170 but downstream the pre-treatment module 160. The valve device 305a and the recirculation path 375 may be included in the RO module 170. A control unit 112 is configured to obtain pressure data, e.g. pressure values, from the pressure sensor 308 and flow rate data, e.g. flow rate values, from the flow rate sensor 309. The data is for example communicated (not shown in figures) by wire or wireless between the control unit 112 and the sensors 308, 309.

Figure 3:
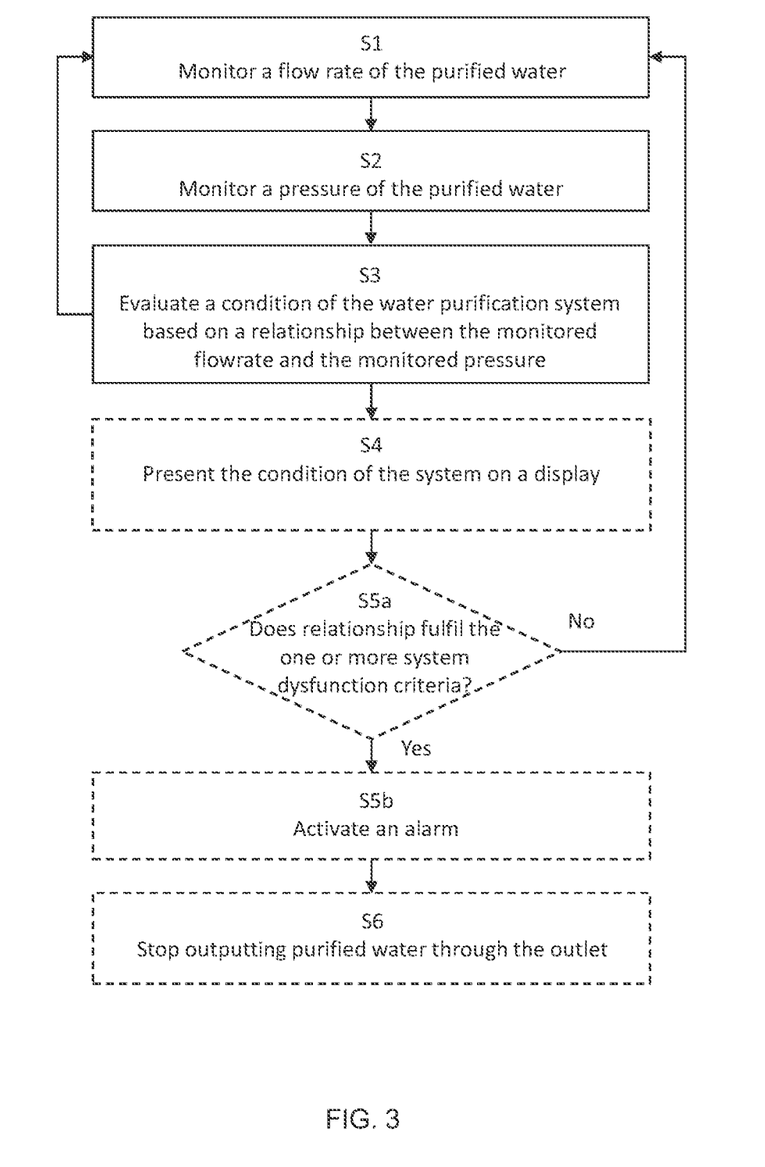
FIG. 3 illustrates a flow chart of a method of evaluating a condition of the water purification system.

In the following a method for evaluating a condition of a water purification system 40, 110 will be explained with reference to the flowchart in FIG. 3 and the diagrams in FIGS. 4-7. The control unit 112 is configured to, or programmed to, perform the method that will be described in the following. The control unit 112 is for example a data processing device comprising means, such as a processor, configured for performing the method that will be described in the following. The control unit 112 also comprises at least one memory for storing one or several programs for performing embodiments of the method, monitored values etc. The method may be embodied as a computer program product comprising instructions which, when the program is executed by the control unit 112, cause the control unit 112 to carry out the method as explained herein. The computer program may be stored on a computer-readable data carrier, for example an external memory device such as an USB (Universal Serial Bus) memory, a portable computer or similar, and loaded into the control unit 112.

The method may be performed during production of purified water, thus on-line. The method comprises monitoring a flow rate S1 correlated with the flow rate of the purified water flowing through the at least one sterilizing grade filter 70a, 70b. For example, the monitoring comprises receiving sensor data from the flow rate sensor 309. The monitoring of a flow rate S1 comprises for example measuring a plurality of flow rate values of the purified water. Thus, in some embodiments the apparatus 110 is arranged to measure a plurality of flow rate values of the purified water, by means of the flow rate sensor 309. The measured values are continually or repetitively received by the control unit 112 as signals, for example by wire. However, the communication of the measured values may also be wireless.

Stated differently, the flow rate sensor 309 measures the flow rate of the purified water in the product fluid path that is the same purified water that is flowing through the one or several sterilizing grade filters 70a, 70b. The flow rate correlated with the flow rate of the purified water flowing through the at least one sterilizing grade filter 70a, 70b then is the direct flow rate of the purified water flowing through the at least one sterilizing grade filter 70a, 70b. The measuring is performed inside the water purification apparatus 110, but the filters 70a, 70b are outside the apparatus 110. Alternatively, the flow rate sensor 309 is measuring on a flow that is not exactly the same as the purified flow through the filters 70a, 70b, but a flow that indicates the flow rate, and thus any changes of the flow rate, through the filters 70a, 70b.

The method also comprises monitoring a pressure S2 correlated with the pressure of the purified water flowing to the at least one sterilizing grade filter 70a, 70b. For example, the pressure sensor 308 measures the pressure of the purified water in the product fluid path that is the same purified water that is flowing to the at least one sterilizing grade filter 70a, 70b. The pressure correlated with the pressure of the purified water flowing to the at least one sterilizing grade filter 70a, 70b then is the direct pressure of the purified water flowing to the at least one sterilizing grade filter 70a, 70b. This pressure also indicates the pressure over the at least one sterilizing grade filters 70a, 70b, and thus any pressure change (drop or increase) over all (one or several) sterilizing grade filters. The monitoring of a pressure S2 comprises for example measuring a plurality of pressure values of the purified water. The monitoring comprises receiving sensor data from the pressure sensor 308. Thus, the apparatus 110 is arranged to measure a plurality of pressure values of the purified water, by means of the pressure sensor 308. The measured values are continually or repetitively received by the control unit 112 as signals, for example by wire. However, the communication of the measured values may also be wireless. The measuring is performed inside the water purification apparatus 110, but the filters 70a, 70b are outside the apparatus 110. Alternatively, the pressure sensor 308 is measuring on water that is not exactly the same as the purified water flowing to the filters 70a, 70b, but a water that indicates the pressure, and thus any changes of the pressure of the water, that is flowing to the filters 70a, 70b.

The method further comprises evaluating S3 a condition of the water purification system based on a relationship between the monitored flow rate and the monitored pressure. A condition is for example that the at least one sterilizing grade filter 70a, 70b leaks, or that the at least one sterilizing grade filter 70a, 70b is clogged. In both cases the bioburden of the water purification apparatus 110 has become too large, as the system 40, 110 will not output purified water as expected according to specifications. For example, if the at least one sterilizing grade filter has a leak the water might not be purified as expected, and if the at least one sterilizing grade filter is clogged, purified water might not be produced in sufficient amounts. The evaluating S3 may include to compare the relationship, or a processed value of the relationship, with one or several thresholds or limits.

The pressure drop over the at least one filter 70a, 70b increases over time as particles are retained on the filter surface and increases the resistance. The permeability of the at least one filter 70a, 70b thus decreases over time. The apparatus 110 may then has to increase the pressure of the product water to maintain a certain flow rate through the at least one filter 70a, 70b. By monitoring the pressure and flow rate, for example over time, the permeability of the filters 70a, 70b may be evaluated. In other words, the relationship between the monitored flow rate and the monitored pressure indicates a permeability property of the at least one sterilizing grade filter 70a, 70b.

The relationship between the monitored flow rate and the monitored pressure may also indicate a bioburden of the water purification apparatus 110. With bioburden is meant the number of microorganism within the feed water per volume, for example per milliliter. If the number of microorganisms is greater than the apparatus 110 can handle, the bioburden of the apparatus 110 is too large. This means that the apparatus 110 cannot purify the feed water to a sufficient purity level, and it will output purified water that contains more microorganism, and thus a larger bioburden, than specified. Thus, it's working load is too large. The functional parts of the apparatus 110 are then not correctly adapted for the contamination degree of the feed water.

The relationship is for example a ratio of monitored flow rate to monitored pressure, Q/P. Alternatively, the relationship is a ratio of monitored pressure to monitored flow rate, P/Q. The monitored flow rate and the monitored pressure are synchronized in time. In some embodiment, the method comprises evaluating S3 the condition of the water purification system based on whether the relationship fulfils one or more system dysfunction criteria. The control unit 112 of the apparatus 110 is configured to perform the evaluation.

A system dysfunction criterion includes for example that the ratio value goes beyond a first ratio limit, or goes beyond a second ratio limit. The first ratio limit is for example an upper ratio limit, and the second ratio limit is a lower ratio limit. The upper ratio limit is greater than the lower ratio limit. A system dysfunction criterion includes for example that the slope value of a curve of the ratio as a function of time goes beyond one or several slope limits. Further system dysfunction criteria will be explained in the following. If one or several system dysfunction criteria is fulfilled, a user may be notified of the condition of the system via an alarm and/or a presentation on a display. The user may also be prompted to change the disposable line set 40. The user will then have the possibility to change the line set to continue the treatment.

Figure 4:
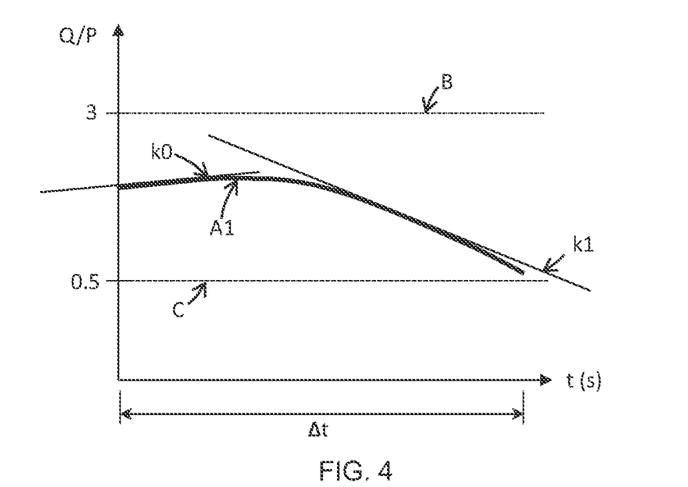
FIGS. 4-7 illustrate a plurality of ratio versus time scenarios.

FIG. 4 illustrates a diagram of a curve A1 of the ratio Q/P as a function of time t. The time period Δt denotes a period of use of a new at least one sterilizing grade filter, for example during which a batch of purified water is prepared. The batch of purified water is according to one embodiment 1-5 liters, for example 2 liters. Purified fluid from the water purification apparatus 110 is then pumped into the line set 40 and thus through the at least one filters 70*a*, 70*b*.

Before the at least one sterilizing grade filter 70*a*, 70*b* is being used, it typically has a temperature of the environment, for example 20° C. The purified water is heated in the water purification apparatus 110 by the heater 302 to a temperature of approximately 30° C. In the beginning of production of purified water, there may thus be a temperature difference between the temperature of the at least one sterilizing grade filter 70*a*, 70*b* and the temperature of the purified water. The at least one sterilizing grade filter 70*a*, 70*b* is slowly warmed to the temperature of the purified water when the purified water is passed through the at least one sterilizing grade filter. When the at least one sterilizing grade filter is warmed, it becomes more permeable and the flow through the at least one sterilizing grade filter increases. The ratio Q/P then increases, as is illustrated in the diagram in FIG. 4 as a small rise of the curve A1 in the beginning of the time period Δt. The positive slope in the beginning is here denotes with k0. Soon the at least one sterilizing grade filter will have the same temperature as the heated purified water, and the permeability of the at least one sterilizing grade filter becomes more or less stable, as can be seen as a crest of the curve A1. Already from the start, the remaining microorganisms in the purified water from the water purification apparatus 110 starts to clog the at least one sterilizing grade filter. The warming of the at least one sterilizing grade filters mitigates and shields this behavior, but as soon as the at least one sterilizing grade filter has the same temperature as of the purified water, the flow through the at least one sterilizing grade filter will slowly decrease and accordingly also the ratio Q/P will decrease, as illustrated in the diagram in FIG. 4. This is an expected behavior of the at least one sterilizing grade filter. The gradient k1 of the curve A1 after the crest may depend on the characteristics of the at least one sterilizing grade filter, the number of microorganisms in the purified water etc. The ratio should be kept within an interval limited by an upper ratio limit B and a lower ratio limit C. Within this interval, the at least one sterilizing grade filter is working as expected and the bioburden on the system is manageable by the system. If the ratio is Q/P, the interval is for example between a lower ratio 0.5 to an upper ratio 3, as illustrated in the figures. The gradient k1 in FIG. 4 may be considered as an expected or normal gradient for the apparatus 110. The curve A1 should thus not go beyond the limits B and C during the time period Δt (period for producing water for at least one treatment) for the system to be considered working properly. A condition of the system may thus be that the system is working properly, thus as expected.

It should be noted that a control goal of the apparatus 110 may be to maintain a predetermined flow rate of the product water. In order to maintain a predetermined flow rate, the apparatus 110 may have to increase (or decrease) the pressure of the product water. However, the pressure is not allowed to increase more than to a predetermined upper pressure level to not cause damage to the filters (or other internal components of the apparatus 110), or decrease without limits, and the interval limits B, C illustrated in the diagrams in FIGS. 4-7 may reflect such limits. The interval limits B, C may for example be determined by experiments or predetermined by the manufacturer.

If the ratio Q/P exceeds the upper ratio limit B, it can be established that the at least one sterilizing grade filter leaks. In case of a leak, the flow through the at least one sterilizing grade filter may increase, and the amplitude of the ratio will then increase. The apparatus 110 may try to maintain a predetermined flow rate of the product water by decreasing the pressure of the product water in order to reduce the flow rate. This will also cause the ratio to increase. In other words, the one or more system dysfunction criteria comprise that the ratio exceeds an upper ratio limit indicating the condition that the at least one sterilizing grade filter leaks. In some embodiments, if several sterilizing grade filters are connected in series, a break-through (i.e. leak) may occur only in one of the sterilizing grade filters, while the other filter(s) is/are without any leaks, and still be detectable. The total pressure fall over the several filters is the sum of the pressure fall over all the filters. If a break-through in one filter occurs, this will decrease the monitored pressure that is correlated with the pressure of the purified water flowing to the filters, as this pressure also indicates the pressure over the filters. The flow rate through the filters will be kept constant. A decreased pressure will also increase the ratio Q/P, even if the flow rate is kept constant, whereby the amplitude of the ratio may increase beyond the upper ratio limit B and thereby it can be established that there is a break-through in at least one of the at least one sterilizing grade filters. As understood, a break-through of two filters out of three filter in series, etc., may give rise to a detectable increase of the ratio Q/P.

If the ratio Q/P exceeds the lower ratio limit C, it can be established that the at least one sterilizing grade filter is clogged. In case of clogging, the flow through the at least one sterilizing grade will decrease, and the amplitude of the ratio will decrease. The apparatus 110 may try to maintain a predetermined flow rate of the product water by increasing the pressure of the product water in order to increase the flow rate. This will also cause the ratio to decrease. In other words, the one or more system dysfunction criteria comprise, that the ratio goes below a lower ratio limit indicating the condition that the at least one sterilizing grade filter 70*a*, 70*b* is clogged and the bioburden of the water purification apparatus is too large.

In one embodiment, the apparatus 110 performs a single startup check of the ratio for product water flowing to the at least one sterilizing-grade filter 70*a*, 70*b*. This may be performed during preparation of the system and prior to the patient is connected to the line set 40. The at least one filter 70*a*, 70*b* is according to one embodiment new with minimal bacteria load. If ratio goes beyond the upper rate limit B, a break-through, or gross integrity breach, is present and the line set 40 should be exchanged. The treatment should thus be restarted with a new line set 40. If the ratio goes beyond the lower rate limit C, the at least one sterilizing grade filter is clogged or in other sense does not let the proper flow through and the line set 40 should be exchanged. The treatment should thus be restarted with a new line set 40.

The ratio in FIGS. 4-7 is here illustrated as Q/P, but could alternatively be P/Q. The curve A1 would then be mirrored and the corresponding limits B, C should be changed accordingly.

Figure 5:
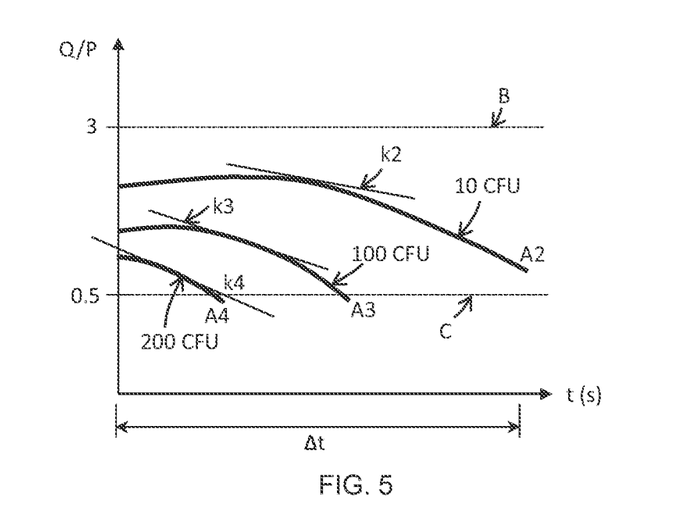

FIG. 5 illustrates a number of curves A2-A4 with corresponding different gradients k2-k4. It is here illustrated that by monitoring the gradient of the curve, an early detection of a condition of the system may be achieved. The curve A2 illustrates a first curve A2 that stays within the interval C-B during the time period Δt, and has a gradient k2. The first curve A2 thus shows that the system has an acceptable bioburden. The curve A3 illustrates another scenario with another at least one sterilizing grade filter giving a second curve A3 that does not stay within the interval C-B during the time period Δt. The second curve has a gradient k3. By comparing the value of the gradient or slope of the curve with one or several limits for the gradient, it can be established that the system does not have an acceptable bioburden, upon the gradient is greater than at least one of the one or several limits. The bioburden of the purified water from the apparatus 110 is here about 100 CFU, which is not acceptable. In other words, the one or more system dysfunction criteria include that the slope value is negative and is less than a first negative slope limit value. Also, the evaluating S3 comprises determining the condition that the at least one sterilizing grade filter 70a, 70b is or will be clogged to a first degree and the bioburden of the water purification apparatus is too large, upon determining that the slope value is negative and is less than the first negative slope limit value. The control unit 112 of the apparatus is configured to perform such evaluating and determining. The first negative slope limit value is for example a percentage deviation from the slope value k1 of the regular curve A1 illustrated in FIG. 4.

FIG. 5 also illustrates another scenario with still another at least one filter resulting in a third curve A4 that also does not stay within the interval C-B during the time period Δt. The third curve A4 has a gradient k4. The gradient k4 is greater and thus steeper than the gradient k3, and the curve A4 crosses the lower limit C sooner in time than the curve A3. The bioburden of the purified water is here about 200 CFU, which is not acceptable. With other words, the one or more system dysfunction criteria include that the slope value is negative and is less than a second negative slope limit value, wherein the second negative slope limit value is less than the first negative slope limit value. The evaluating S3 then comprises determining the condition that the at least one sterilizing grade filter 70a, 70b is or will be clogged to a second degree and the bioburden of the water purification apparatus is too large, upon determining that the slope value is negative and is less than the second negative slope limit value. The control unit 112 of the apparatus 110 is configured to perform the evaluating and the determining. The second negative slope value is thus greater than the first negative slope value. Thus, the method continuously calculates and evaluates the slope of the ratio function, and compares the slope value with limit values, to detect any dysfunction. The line set 40 may then be exchanged at an early stage, or it can early be established that the feed water is to dirty to clean for the water purification apparatus 110, if any dysfunction is early detected.

Thus, by monitoring and evaluating the slope of the curve of a function of the ratio Q/P (or P/Q), a condition of the system can be established. In other words, in some embodiments the evaluating S3 comprises determining a slope value of a curve of a function of a ratio of monitored flow rate to monitored pressure, and wherein the one or more system dysfunction criteria comprises that the slope value goes beyond one or more slope limit values. The control unit 112 of the apparatus 110 is configured to perform such an evaluation.

The control unit 112 continuously monitors the slope over time of the ratio as product water flows to the at least one sterilizing grade filter. Thus, the control unit 112 monitors the slope during actual production of purified water for a treatment. This may occur both before a patient has been connected to the line set 40, after the patient has been connected to the line set 40 or during a patient is being connected to the line set 40. The monitoring is thus performed during a treatment of a patient, that includes to prepare one or several batches of purified water.

Figure 6:
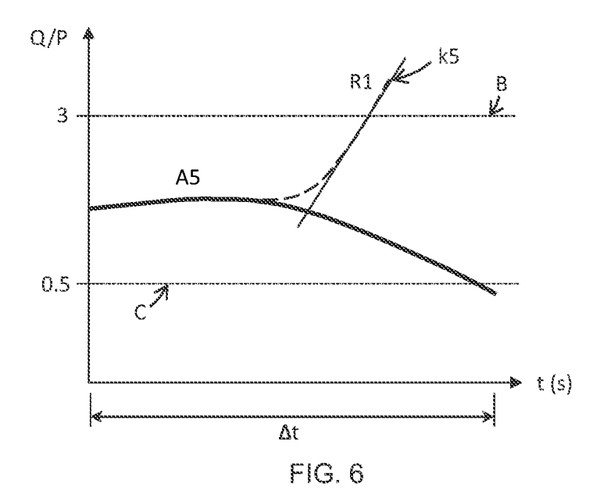

FIG. 6 illustrates a curve A5 of the ratio over time, and with a dashed line, the behavior of the ratio during a break-through of the at least one sterilizing grade filter. The solid line denotes the regular expected behavior of the system. Again, it is the ratio Q/P that is monitored, but it could alternatively be the ratio P/Q. If a break-through in all of the at least one sterilizing grade filter occurs, the flow rate of the purified water flowing through the at least one sterilizing grade filter will increase and the pressure of the purified water upstream the at least one sterilizing grade filter will decrease. Thereby the ratio Q/P will increase, as shown in the FIG. 6. In such scenario, the ratio may go beyond the upper limit B, and thus trigger the determination that the condition that the at least one filter 70a, 70b leaks. The slope k5 of the curve is thus positive. If a break-through in all of the at least one sterilizing grade filter occurs, it is expected that the flow rate increases rapidly, and thus the curve will get a steep positive slope that indicates the break-through. If the slope k5 increases more than a certain slope limit, it can be established that a break-through has occurred. A break-through may occur in only a subset, e.g. one of the sterilizing grade filters, if there are several filters, and still be detectable. For example, if the line set, e.g. the upstream water line segment 64a, comprises two sterilizing grade filters 70a, 70b in series, only one of the filters needs to have a break-through and still the breakthrough may be detectable, of course also depending on the size of the break-through. This because a break-through will cause a pressure drop that is detectable by the pressure monitoring. The flow rate through the filters may then not increase, but as the pressure decreases, the ratio Q/P will increase. A breakthrough in each (e.g. here both) of the filters will cause both an increased flow rate through the filters and a pressure drop, that together will increase the ratio Q/P. Thus, by monitoring and evaluating the slope of the curve, a break-through can be detected. In other words, the one or more system dysfunction criteria include that the slope value is positive and is greater than a positive lower slope limit value, and wherein the evaluating S3 comprises determining the condition that the at least one sterilizing grade filter 70a, 70b leaks, upon determining that the slope value is positive and is greater than the positive lower slope limit value. The control unit 112 of the apparatus 110 is configured to perform such determining. The limit values may for example be determined by experiments.

Figure 7:
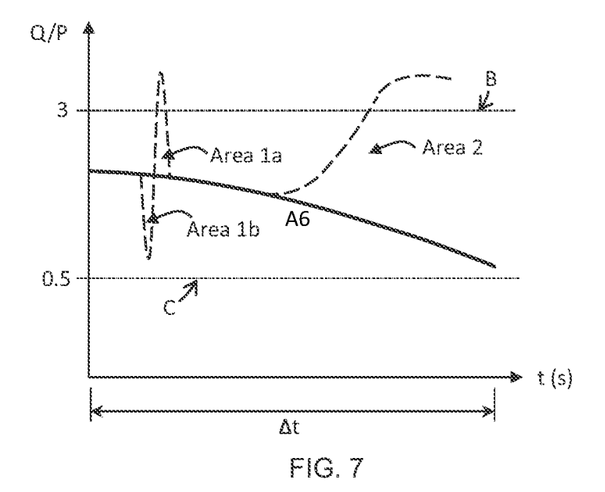

FIG. 7 illustrates a curve A6 of the ratio over time, and further scenarios in dashed lines, where the flow of purified water is temporarily stopped and then started again, for example by accident when someone accidently steps upon the line set 40, and a following break-through of the at least one sterilizing grade filter. The solid line illustrates the regular curve if the system is working properly. The temporary stop of the purified water flow is illustrated as a rapid and steep oscillation, where the flow rate is stopped and the ratio then decreases, and a following increase in flow rate where the ratio then increases when the flow is allowed again, all during a short period of time, e.g. 1-3 seconds. Thereafter the purified water resumes its regular flow rate. Such an incident should not trigger any alarm, and should thus be neglected in the evaluation of the condition of the system. Each deviation from the regular curve gives rise to an area above or below the curve. By evaluating the area or areas of an incident, it can be determined if the incident should affect the condition of the system. The evaluation may include to sum the areas of an incident, for example sum the positive area 1a and the negative area 1b of the curve of the oscillation. It can be assumed that such an oscillation will have a sum of zero, close to zero, or at least a sum that is smaller or equal to a positive area limit value. By identifying such condition, the incident can be neglected in the present evaluation of a condition of the system. Thus, the evaluation S3 may include to identify an oscillation by calculating a sum of one or several areas of a curve of a function of ratio values of monitored flow rate to monitored pressure versus time, and if the sum is smaller or equal to a positive area limit value, an oscillation is identified and the method comprises neglecting the oscillation in the evaluation S3. The control unit 112 of the apparatus 110 is configured to perform the calculating, identification and neglecting.

If an actual break-through occurs, the curve will raise as shown in the right-hand side of the diagram of FIG. 7 by the dashed line and thus deviate from the regular shape of the curve illustrated by the solid line curve. If the break-through does not gradually becomes larger, the ratio will stabilize at a higher level to slowly begin to decrease again as the at least one filter continues to become clogged at other parts of the at least one filter than where the break-through is located. The dashed curve now gives rise to an area A2 above the regular curve, the area A2 being limited by the expected behavior (the regular curve given by the solid line curve) and the actual behavior (dashed curve). The method here comprises to determine the area A2. The area A2 is also limited to the right-hand side by an imaginary vertical line from where the dashed curve ends to the regular curve. The expected behavior (the regular curve) of the system may be determined in beforehand or simulated/calculated during performance of the method. Here, the one or more system dysfunction criteria includes that the area is greater than a positive area limit value. The method also comprises determining the condition that the at least one filter 70a, 70b leaks, upon determining that the area is greater than the positive area limit value. The positive area limit value is chosen such that an oscillation is surely neglected. The control unit 112 of the apparatus 110 is configured to perform such determining.

Alternatively, an accidental oscillation can be identified or neglected in other ways. For example, if an oscillation occurs, the ratio before the oscillation is more or less the same as the ratio after the oscillation. However, if a break-through occurs, the ratio before the break-through will differ significantly from the ratio when the flow rate has stabilized after the break-through occurred. In other words, the evaluating S3 comprises detecting a change of the ratio above a predetermined level and determining whether the ratio before the change is equal within an interval to the ratio after the change. Upon determining that the ratio before the change is not equal within an interval to the ratio after the change, the method comprises determining the condition that the at least one filter 70a, 70b leaks. Thereby irrelevant incidents for evaluating a condition of the system can be neglected in the evaluation. The control unit 112 of the apparatus 110 is configured to perform such evaluating and determining. The interval is typically a small value, e.g. 1-5% of the ratio value.

It is desired to monitor the condition of the system, and for that purpose the method may comprise presenting S4 the condition of the water purification system on a display 120. The control unit 112 may be configured to present the condition of the water purification system, for example on the display 120 of the water purification apparatus 110. The presentation of the condition may be accompanied with a presentation of an action that the user should perform, for example stop water production and/or change the currently used line set 40 for a new line set. For that purpose, the control unit 112 is connected to the display by wire or wirelessly. The display is for example a display of the water purification apparatus 110, a display of the cycler, or another external display such as a display of a mobile phone or a computer. The condition may be continuously displayed, or may be displayed upon the relationship fulfils one or more of the system dysfunction criteria. To get attention to a change of a condition of the system, for example that the relationship fulfils the one or more dysfunction criteria, the method in some embodiments comprises activating S5 an alarm upon the relationship fulfils one or more system dysfunction criteria. Thus, the control unit 112 is configured to activate an alarm upon the relationship fulfils one or more system dysfunction criteria. The alarm may be generated as sound via a loudspeaker, as vibration via a tactile means or as a message on a display. The alarm may be generated from the apparatus 110 itself, or generated from a remote unit such as a mobile phone or a computer belonging the user of the apparatus 110. The user will then be aware of that the system is not working correctly.

As fulfillment of dysfunction criteria indicates a dysfunction of the system and that the system may not purify the water to a sufficient purity, the method may include stopping S6 outputting purified water through the outlet port 128 upon the relationship fulfils one or more system dysfunction criteria. Thereby it is hindered that the system 110, 40 will deliver water with an insufficient purity or to an insufficient amount. Thus, in some embodiments, the apparatus 110 is arranged to stop outputting purified water through the outlet port 128 upon the relationship fulfils one or more system dysfunction criteria. Hence, if the water cannot be purified properly or not to a sufficient amount, the apparatus 110 stops the production of purified water. The apparatus 110 may stop outputting purified water by closing the valve 305d (see FIG. 8) and/or stopping the RO-pump 450.

Detailed Description of a Water Purification Apparatus

Figure 8:
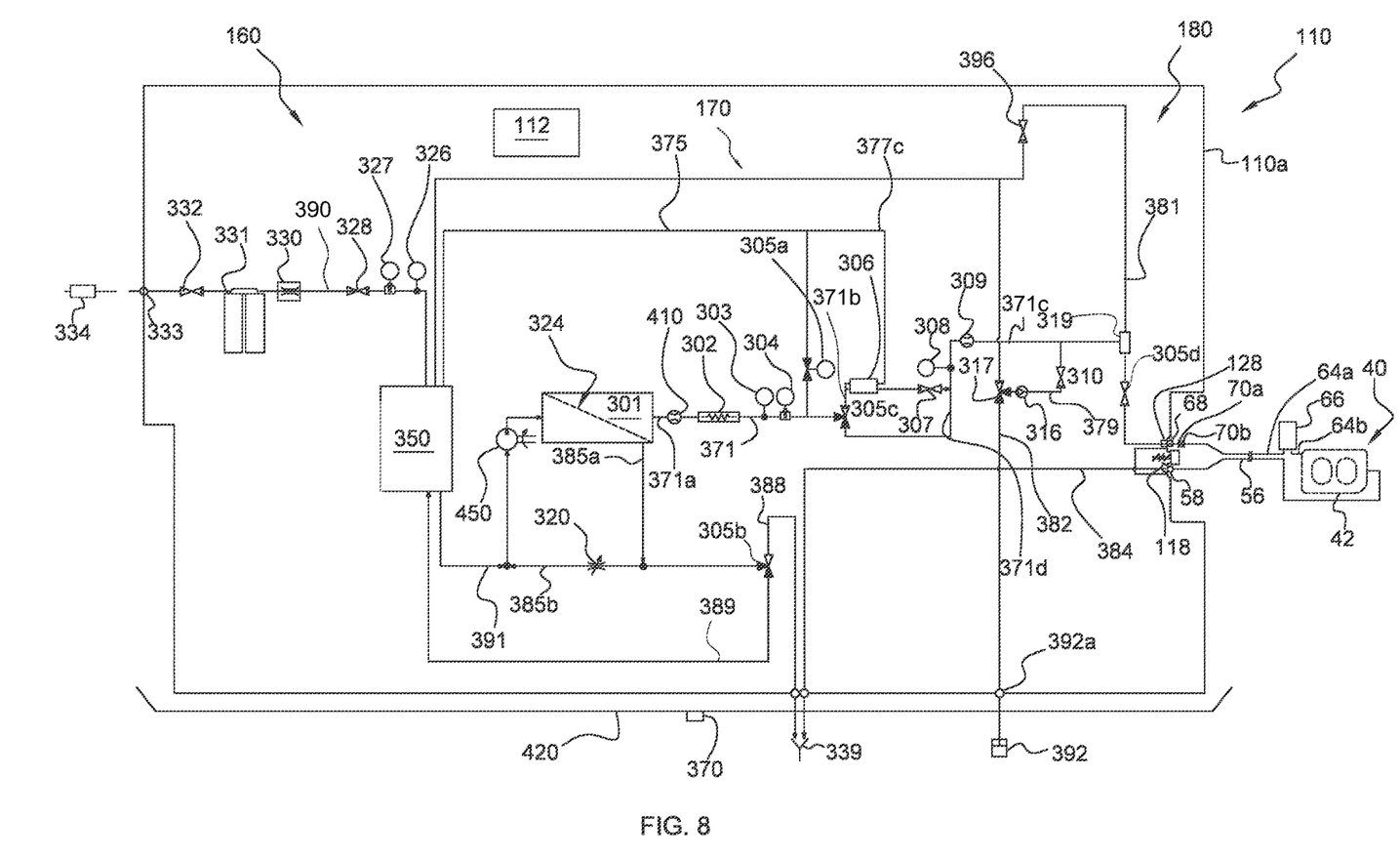
FIG. 8 illustrates a water purification apparatus connected to a fluid line set according to one embodiment.

FIG. 8 illustrates an example embodiment of the water purification apparatus 110. The water purification apparatus 110 receives water from a water source, such as a continuous source of potable or drinkable water from a patient's home. In various embodiments, water purification apparatus 110 may be installed in a room having access to the water source to provide water for PD to cycler 20 as discussed herein. The water is optionally filtered using a particle pre-filter 334 to remove dirt and sediment, before it is delivered to the water purification apparatus 110. The water enters the water purification apparatus 110 via the water inlet port 333. As previously described, the water purification apparatus 110 includes a pre-treatment module 160, a RO module 170 and a post-treatment module 180. The pre-treatment module 160 includes a particle filter and an activated carbon filter, i.e. an activated carbon bed, to further remove contaminants and impurities. The particle filter and the activated carbon filter are embodied in one single filter package 331. The single package 331 is a disposable package. The pre-treatment module 160 includes an inlet valve 332 and a constant flow device 330 upstream the filter package 331. The inlet valve 332 controls the feed water inflow by control of the control unit 112. The constant flow device 330 provides a constant flow to the tank 350 provided that the water pressure is above a minimum pressure for constant flow device 330. Further, pre-treatment module 160 comprises a tank valve 328, a pre-treatment conductivity sensor 327 and a feed water temperature sensor 326 downstream the filter package 331. The tank valve 328 controls the flow of filtered feed water to the tank 350. The pre-treatment conductivity sensor 327 monitors the conductivity of the filtered feed water, and the feed water temperature sensor 326 monitors the temperature of the filtered feed water. The temperature of the filtered feed water is for example needed to calibrate the conductivity measurement of the filtered feed water. The described components are included in a pre-treatment fluid path 390. The pre-treatment fluid path 390 is connected to the water inlet port 333 and ends into the tank 350. The inlet valve 332 and the tank valve 328 are configured to be controlled by the control unit 112 of the water purification apparatus 110. It should be appreciated that the filter package 331 is in some embodiments not required and may not be present.

The RO module 170 comprises the tank 350, the RO-pump 450 and the RO-device 301. The filtered (or unfiltered) feed water enters the tank 350, for example from an upper part of the tank 350. Feed water is accumulated in the tank 350 and pumped by the RO-pump 450 to a feed inlet of the RO-device 301. A feed path 391 connects the tank 350 with the RO-device 301. The RO-pump 450 is fitted to the feed path 391.

Empty, low and high-level switches (not shown) provided in tank 350 detect its water level, while a computer program running on the control unit 112 of the water purification apparatus 110 is configured to control the opening and closing of inlet valve 332 and tank valve 328, which are open during the filling of tank 350, and closed when the water level in tank 350 activates its high-level switch connected to control unit 112. Inlet valve 332 opens again when the water level falls below low-level switch of tank 350, thus tripping the low-level switch connected to control unit 112. If the water level in the tank 350 rises too high, excess water is drained via an overflow connection (not shown), e.g. to a tray 420 or drain 339.

The control unit 112 is configured to cause RO-pump 450 to stop pumping, if empty level switch in tank 350 detects air or a critically low water level. RO-pump 450 is configured to provide the water flow and pressure requisite for the reverse osmosis process taking place at RO-device 301. The RO-device 301 filters water using a RO-membrane 324 to provide purified water at its permeate outlet. Reject water is leaving RO-device 301 at a reject outlet (may be fed back into RO-pump 450 to conserve water consumption or alternatively be pumped to drain 339.)

Purified water leaving the RO-device 301 is transported in a purified fluid path 371 inside the water purification apparatus 110 before being output through an outlet port 128, thus a water outlet. The purified fluid path comprises permeate fluid path 371a, polisher fluid path 371b and product fluid path 371c. The EDI-device 306 may be by-passed via the bypass path 371d. The bypass path 371d is connected to the fluid path upstream the EDI-device 306, and to the fluid path downstream the EDI-device 306. Purified water leaving the RO-device 301 passes a flow sensor 410, a heater 302, and a permeate temperature sensor 303, arranged to the permeate fluid path 311a. The flow sensor 410 monitors the flow of the purified fluid leaving the RO-device 301. The heater 302, heats, by control of the control unit 112, the purified water leaving the RO-device 301. The permeate temperature sensor 303 monitors the temperature of the purified fluid leaving the RO-device 301 directly downstream the heater 302. An additional conductivity sensor 304 monitors the conductivity of purified water leaving RO-device 301.

Downstream the heater 302, the permeate temperature sensor 303 and the additional conductivity sensor 304, the purified fluid enters the post-treatment module 180 via the polisher fluid path 371b. The post-treatment module 180 comprises a polisher device, e.g. the EDI-device 306. The three-way valve 305c is arranged to be controlled by the control unit 112 to selectively direct the purified fluid flow into either the polisher fluid path 371b, or into the bypass path 371d in order to bypass the EDI-device 306. When directed to the EDI-device 306, the purified fluid enters channels of the EDI-device 306, thus product channels, concentrate channels and the electrode channels. The purified fluid is fed to all the channels via the polisher fluid path 371b downstream the three-way valve 305c. The EDI-device 306 is configured to produce product water. The produced product water leaves the EDI-device 306 and enters the product fluid path 371c. A product channel valve 307 regulates the flow rate of the product water in the product fluid path 371c from the product channel of the EDI-device. A concentrate fluid path 377c is arranged to pass concentrate water and electrode fluid from the EDI-device 306 back to the tank 350.

The product water is passed to the outlet port 128, and further into a thereto connected water line 64 (64a, 64b) of the fluid line set 40 for transport to the point of treatment, connected via a water line connector 68 to the outlet port 128. The at least one sterilizing grade filters 70a, 70b filter the product water leaving the outlet port 128 into sterilized product water, that is suitable for injection.

A drain port. 118 defines a first drain path 384 to the drain 339. A drain line 56 of the fluid line set 40 is connected to the drain port 118 via a drain line connector 58, in order to pass fluid, such as used PD-fluid, from the drain port 118 to the drain 339. The first drain path 384 here embodies the part of a cycler drain path that is present inside the water purification apparatus 110.

The flow control device 305a is configured to control the flow rate of purified water in a recirculation path 375 arranged from a point downstream the heater 302, the permeate temperature sensor 303 and the additional conductivity sensor 304, and back to the tank 350. A product water pressure sensor 308 is arranged to monitor the pressure in the product fluid path 371c downstream the EDI-device 306. A product water flow sensor 309 is arranged to monitor the flow rate of the product water downstream the EDI-device 306. The pressure and the flow rate of the product water are feed to the control unit 112. The control unit 112 is configured to control the operation of the flow control device 305a. More particularly the control unit 112 is configured to regulate the flow rate in the recirculation path 375 based on the pressure and flow rate of the product water, in order to control the flow rate of the product water to a desired flow rate, and the pressure of the product water to a desired pressure. The flow control device 305a is for example a motorized flow control valve that is configured to finely regulate the flow rate in the recirculation path 375.

A product water valve 305d is arranged to, by control of the control unit 112, control the produced product flow to go to either the outlet port 128, or back to the tank 350 via an additional recirculation path, here a first recirculation path

381. An emptying valve 396 is arranged to control the flow rate in the first recirculation path 381. The first recirculation path 381 is fluidly connected to the product fluid path 371c via an air-trap chamber 319. A product water conductivity sensor (not shown) may be arranged to monitor the conductivity of the product water, e.g. upstream the air-trap chamber 319. A product fluid temperature sensor (not shown) may be configured to monitor the temperature of the product water, e.g. upstream the air-trap chamber 319.

In operation, a portion of the rejected water leaving the RO-device 301 via a fluid path 385a passes an auxiliary constant flow device (not shown), which provides a steady flow of rejected water to a three-way valve 305b (e.g. a three-way solenoid valve) under control of control unit 112. A remaining portion of the rejected water returns to RO-pump 450 via a valve 320 (e.g. a manual needle valve) in a first reject path 385b. Three-way valve 305b is configured to selectively divert the rejected water either to drain 339 via a second drain path 388 or back to tank 350 via a second reject path 339.

All meters and sensors described in connection with water purification apparatus 110 in FIG. 8 are configured to communicate their corresponding signals, e.g. measured quantities, to control unit 112.

The water purification apparatus 110 includes a container 392 containing a microbiological growth inhibiting agent. As illustrated, container 392 is in fluid communication with an inlet 392a of the water purification apparatus 110. In FIG. 8, a chemical intake path 382 connects container 392 to the fluid paths of the water purification apparatus 110. Alternatively, container 392 may be connected via a line (not illustrated) leading directly to disposable cassette 42 operating with cycler 20, or be connected to water line 64, or be connected to drain line 56.

The agent inhibiting microbiological growth in the container 392 may be a suitable physiologically safe acid, such as citric acid, citrate, lactic acid, acetic acid, or hydrochloric acid (or a combination thereof). In one embodiment, container 392 contains citric acid, citrate or a derivative thereof. It is noted that container 392 may also include additives provided together with the acid (such as with citric acid). The chemical inlet 392a, is located for example at the front of water purification apparatus 110. A presence sensor (not shown, e.g. an optical sensor) is arranged to sense when the container 392 is connected to the chemical inlet 392a. A three-way valve 317, under control of control unit 112, connected with chemical inlet 392a is arranged to open towards a second pump 316 being a chemical intake pump and tank 350. The second pump 316 is arranged to feed disinfecting solution into tank 350. The second pump 316 and a valve 310 are arranged in a path 379 fluidly connecting the three-way valve 317 and the product fluid path 371c. The valve 310 is arranged to control the flow in the path 379.

The described pre-treatment module 160, the RO module 170 and post-treatment module 180, are enclosed inside of a single water purification cabinet 110a, except for the filter package 331, which is removably arranged, e.g. hinged, on the outside of the single water purification cabinet 110a. The filter package 331 may then be exchanged when exhausted. In an alternative embodiment, the modules may be arranged in separate units. As mentioned above, purified water is sent from water purification apparatus 110 to disposable set 40 via water line 64. Referring to FIG. 1, water line 64 feeds purified water to a water port of cassette 42 of disposable set 40. Water line 64 is in one embodiment a flexible tube having a first end connected to the outlet port 128 of the water purification apparatus 110 and a second end connected to a water port of the cycler 20. Water line 64 may be at least 2 meters long and in one embodiment longer than 4 meters. Water line 64 allows water purification apparatus 110 to be installed in a room having an available water source, while cycler 20 resides in a different room in which the patient resides, e.g., sleeps. Water line 64 may accordingly be as long as necessary to connect water purification apparatus 110 to cycler 20.

FIG. 8 also illustrates that the disposable line set 40 includes a drain line 56 configuration arranged to conduct fluid, such as used dialysis fluid, to the drain 339 of the water purification apparatus 110. Drain line 56 is e.g. a tube having a first end connected to cassette 42 of cycler 20 and a second end including a drain line connector 58 connected to a drain port 118 of the water purification apparatus 110. Drain line 56 may alternatively be a flexible tube, which may be more than 2 meters long and in some embodiments longer than 4 meters. Drain line 56 may be as long as necessary to connect between water purification apparatus 110 and cycler 20. Water line 64 and drain line 56 in the illustrated embodiment run parallel using dual lumen tubing. It is also possible that water purification apparatus 110 and cycler 20 are positioned close together, such that the same two or double line fluid path including water line 64 and drain line 56 may for example be less than 0.5 meters. Moreover, while a dual lumen water line 64 and the drain line 56 are illustrated, it is possible that water line 64 and drain line 56 are separate.

A water tray 420 is positioned below the water purification apparatus 110. A liquid sensor 370 is arranged at the bottom of the water tray 420 to detect any leakage from the water purification apparatus 110. In one example embodiment, the water tray 420 is enclosed inside the purification cabinet 110a of the water purification apparatus 110.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A water purification apparatus arranged to output purified water through an outlet port and through at least one sterilizing grade filter of a line set fluidly connected to the outlet port, the water purification apparatus comprising a control unit configured to:
monitor, by means of a flow rate sensor that is located fluidly upstream from the at least one sterilizing grade filter, a flow rate that is correlated with a flow rate of the purified water flowing through the at least one sterilizing grade filter;
monitor, by means of a pressure sensor that is located fluidly upstream from the at least one sterilizing grade filter, a pressure that is correlated with a pressure of the purified water flowing to the at least one sterilizing grade filter; and
evaluate a condition of the water purification apparatus and/or the at least one sterilizing grade filter based on whether a relationship between the monitored flow rate and the monitored pressure exceeds one or more limits indicating one or more system dysfunction criteria is fulfilled, wherein the relationship is:
(i) a ratio of the monitored flow rate to the monitored pressure, wherein:
a first system dysfunction criteria of the one or more system dysfunction criteria is fulfilled when the ratio exceeds an upper ratio limit of at least 3, fulfillment of the first system dysfunction criteria indicating that the at least one sterilizing grade filter leaks, and a second system dysfunction criteria of the one or more system dysfunction criteria is fulfilled when the ratio falls below a lower ratio limit of at least 0.5, fulfillment of the second system dysfunction criteria indicating that the at least one sterilizing grade filter is clogged and a bioburden of the water purification apparatus is too large, or (ii) a slope value of a curve of a function of a ratio of the monitored flow rate to the monitored pressure versus time, wherein the slope value extending beyond one or more slope limit values indicates another system dysfunction criteria of the one or more system dysfunction criteria is fulfilled.

2. The water purification apparatus according to claim 1, wherein the relationship indicates a permeability property of the at least one sterilizing grade filter and/or the bioburden of the water purification apparatus.

3. The water purification apparatus according to claim 1, wherein the one or more system dysfunction criteria includes a third system dysfunction criteria, and wherein the third system dysfunction criteria is fulfilled when the slope value is positive and is greater than a positive lower slope limit value, and wherein the control unit is configured to:
determine the condition that the at least one sterilizing grade filter leaks, upon determining that the slope value is positive and is greater than the positive lower slope limit value.

4. The water purification apparatus according to claim 1, wherein the one or more system dysfunction criteria includes a fourth system dysfunction criteria, and wherein the fourth system dysfunction criteria is fulfilled when the slope value is negative and is less than a first negative slope limit value, and wherein the control unit is configured to:
determine the condition that the at least one sterilizing grade filter is or will be clogged to a first degree and the bioburden of the water purification apparatus is too large, upon determining that the slope value is negative and is less than the first negative slope limit value.

5. The water purification apparatus according to claim 4, wherein the one or more system dysfunction criteria includes a fifth system dysfunction criteria, and wherein the fifth system dysfunction criteria is fulfilled when the slope value is negative and is less than a second negative slope limit value, wherein the second negative slope limit value is less than the first negative slope limit value, and wherein the control unit is configured to:
determine the condition that the at least one sterilizing grade filter is or will be clogged to a second degree and the bioburden of the water purification apparatus is too large, upon determining that the slope value is negative and is less than the second negative slope limit value.

6. The water purification apparatus according to claim 1, wherein the water purification apparatus is arranged to measure a plurality of flow rate values of the purified water via one or more sensors including the flow rate sensor.

7. The water purification apparatus according to claim 1, wherein the water purification apparatus is arranged to measure a plurality of pressure values of the purified water.

8. The water purification apparatus according to claim 1, wherein the control unit is configured to present the condition of the water purification apparatus on a display.

9. The water purification apparatus according to claim 1, wherein the control unit is configured to activate an alarm upon the relationship fulfilling at least one of the one or more system dysfunction criteria.

10. The water purification apparatus according to claim 1, wherein the control unit is configured to stop the output of the purified water through the outlet port upon the relationship fulfilling at least one of the one or more system dysfunction criteria.

11. A water purification apparatus arranged to output purified water through an outlet port and through at least one sterilizing grade filter of a line set fluidly connected to the outlet port, the water purification apparatus comprising a control unit configured to:
monitor, by means of a flow rate sensor that is located fluidly upstream from the at least one sterilizing grade filter, a flow rate that is correlated with a flow rate of the purified water flowing through the at least one sterilizing grade filter;
monitor, by means of a pressure sensor that is located fluidly upstream from the at least one sterilizing grade filter, a pressure that is correlated with a pressure of the purified water flowing to the at least one sterilizing grade filter; and
evaluate a condition of the water purification apparatus and/or the at least one sterilizing grade filter based on whether a relationship between the monitored flow rate and the monitored pressure exceeds an upper ratio limit of at least 3 or falls below a lower ratio limit of at least 0.5 indicating a system dysfunction criteria of one or more system dysfunction criteria, wherein the relationship is a ratio of the monitored flow rate to the monitored pressure.

12. The water purification apparatus according to claim 11, wherein the relationship indicates a permeability property of the at least one sterilizing grade filter and/or a bioburden of the water purification apparatus.

13. The water purification apparatus according to claim 11, wherein the control unit is configured to:
evaluate the condition based on whether the relationship fulfils one or more of the system dysfunction criteria.

14. The water purification apparatus according to claim 13, wherein the one or more of the system dysfunction criteria comprises that the ratio exceeds the upper ratio limit indicating the condition that the at least one sterilizing grade filter leaks, or falls below the lower ratio limit indicating the condition that the at least one sterilizing grade filter is clogged and a bioburden of the water purification apparatus is too large.

15. The water purification apparatus according to claim 11, wherein the water purification apparatus is arranged to measure a plurality of flow rate values of the purified water via one or more sensors including the flow rate sensor.

16. The water purification apparatus according to claim 11, wherein the water purification apparatus is arranged to measure a plurality of pressure values of the purified water.

17. The water purification apparatus according to claim 11, wherein the control unit is configured to present the condition of the water purification apparatus on a display.

* * * * *